United States Patent [19]
Thyrion et al.

[11] Patent Number: 5,739,331
[45] Date of Patent: Apr. 14, 1998

[54] PROCESS FOR CONVERTING A XANTHINE RING OR XANTHINE RING DERIVATIVES INTO DIALKYLAMINOXANTHINE DERIVATIVES

[75] Inventors: Fernand Thyrion, Mont-Saint-Guibert; Hong Yang, Louvain-la-Neuve; Michel Parmantier, Brussels, all of Belgium

[73] Assignee: S.A. Nycomed Christiaens N.V., Brussels, Belgium

[21] Appl. No.: 492,046

[22] PCT Filed: Jan. 19, 1994

[86] PCT No.: PCT/BE94/00006
§ 371 Date: Sep. 29, 1995
§ 102(e) Date: Sep. 29, 1995

[87] PCT Pub. No.: WO94/17064
PCT Pub. Date: Aug. 4, 1994

[30] Foreign Application Priority Data
Jan. 21, 1993 [BE] Belgium .................. 9300059

[51] Int. Cl.$^6$ .................. C07D 473/08
[52] U.S. Cl. .................. 544/272

[58] Field of Search .................. 544/272

[56] References Cited

PUBLICATIONS

Van Nostrand's Scientific Encyclopedia (7th Edition) (1995), pp. 18–19.
March, "Advanced Organic Chemistry" (1968), pp. 217–221.

*Primary Examiner*—Mark L. Berch
*Attorney, Agent, or Firm*—Sughrue, Mion, Zinn, Macpeak & Seas, PLLC

[57] ABSTRACT

The invention relates to a process for the preparation of bamifylline or etamiphylline, in which a mixture comprising:

a) theophylline or 8-benzyltheophyl-line;
b) an alkyl dihalide; and
c) a molar excess of an amine is reacted in the presence of a weak base, the reaction being carried out at a temperature higher than 90° C. and under a pressure higher than $10^5$.

15 Claims, No Drawings

PROCESS FOR CONVERTING A XANTHINE RING OR XANTHINE RING DERIVATIVES INTO DIALKYLAMINOXANTHINE DERIVATIVES

The subject of the present invention is a process for the preparation of a compound of formula:

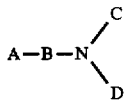

in which

A is a xanthine ring or a compound comprising a xanthine ring (a xanthine ring derivative), B is a hydrocarbon group, C and D are identical or different hydrocarbon groups optionally bearing one or more hydroxyl groups, or of a salt of such a compound. In this process, a xanthine ring or a xanthine ring derivative is reacted with a molar excess of a substance $X_1$—B—$X_2$ where $X_1$ and $X_2$ are electrophilic groups, in the presence of a molar excess of an amine of formula:

and the compound formed is optionally converted into a salt thereof.

THE PRIOR ART

It is known from Belgian Patent BE-A-602,888 to prepare bamifylline, namely a compound of formula II.

According to this patent, bamifylline is prepared by reacting, in a first step, 8-benzyltheophylline with 1,2-dichloroethane or 1,2-dibromoethane to give 7-(β-chloro- or β-bromoethyl)-8-benzyltheophylline (formula I).

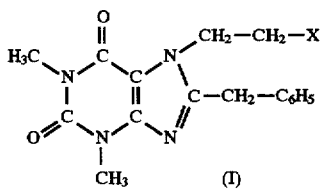

X = Cl or Br

In a second step, the product (I) is reacted with 2-ethylaminoethanol in the presence of sodium carbonate, to form bamifylline (II) in a yield of 57 to 65% according to the following scheme:

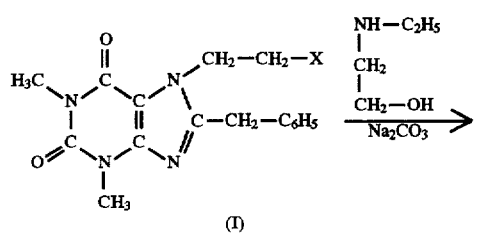

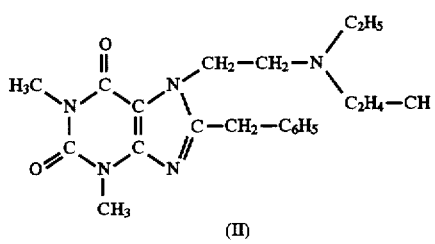

This reaction gives rise to the formation of the derivative 7-vinyl-8-benzyltheophylline (III) as side product, in a large amount (25 to 43%).

It is known from Belgian Patent BE-A-883,654 to prepare bamifylline in a single step with good yield by heating to reflux a reaction mixture consisting of 8-benzyltheophylline, N-ethylaminoethanol, sodium carbonate and 1,2-dichloroethane.

This process, which makes it possible to avoid the formation of the vinyl side product (III),

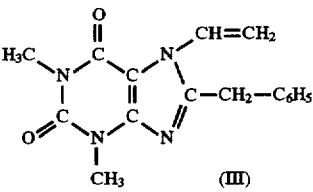

has, however, the drawbacks of a very long reaction time (52 hours) and of formation of about 7% of the derivative 7-chloroethyl-8-benzyltheophylline (I) as side product. The reaction temperature in the process according to this patent is 80° C.

In the process according to the invention, the reaction is carried out at a temperature above 90° C. and at a pressure above $10^5$ Pa.

It has been noted that the process according to the invention allowed the rate of conversion of the nucleophilic ring to be increased, and quite unexpectedly allowed an excellent selectivity to be obtained for the conversion of the xanthine ring or of the xanthine derivative into

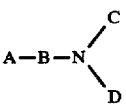

Although a person skilled in the art might have expected that the rate of the 8-benzyltheophylline+N-ethylaminoethanol+1,2-dichloroethane reaction at 90° C. would be greater than the rate of this reaction at 80° C., the person skilled in the art could not expect that the process according to the invention would make it possible furthermore to ensure a selectivity of greater than 90% for the reaction to give bamifylline. The reason for this is that those skilled in the art know that by increasing the temperature of a reaction, not only is the desired reaction promoted, but so are side reactions giving unwanted side products.

Thus, quite unexpectedly, it has been noted that by applying the process according to the invention to the manufacture of bamifylline (8-benzyltheophylline+N-ethylaminoethanol+1,2-dichloroethane), it has been possible to obtain an 8-benzyltheophylline conversion of greater than 99%, after a reaction time of 2 to 5 hours (instead of 52 hours for the process according to BE-A-883,654) and a molar yield of bamifylline relative to the number of moles of 8-benzyltheophylline of greater than 90%, or even higher (>95%).

BRIEF DESCRIPTION OF THE INVENTION

The invention relates to a process for the preparation of a compound selected among the group consisting of bamifylline and etamiphylline, in which a mixture comprising:

a) a compound selected among the group consisting of theophylline and 8-benzyltheophylline;

b) an alkyl dihalide with a number of carbon atom equal to 2 or 3;

c) a molar excess of an amine of formula

with C and D selected among the group consisting of hydrocarbon groups containing and one hydroxyl group and hydrocarbon groups containing from 1 to 4 carbon atoms and two hydoxyl groups
is reacted in the presence of a weak base, the said reaction being carried out at a temperature higher than 90° C. and under a pressure higher than $10^5$ Pa.

Advantageously, the reaction is carried out at a temperature above 110° C., preferably at 125° C.

According to one embodiment of the process according to the invention a xanthine ring or a xanthine ring derivative such as benzyltheophylline or theophylline is reacted with a substance $X_1$—B—$X_2$ in which $X_1$ and $X_2$ are halogen atoms, B is a hydrocarbon group containing from 1 to 5 and preferably 2 or 3 carbon atoms, in the presence of an amine

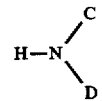

in which C and D are chosen from hydrocarbon groups containing from 1 to 4 carbon atoms and optionally containing up to 2 hydroxyl groups.

According to a particular feature of this embodiment, 8-benzyltheophylline is reached with an alkyl dihalide, in particular dichloroethane and/or dichloropropane, in the presence of an alkylaminoalkanol.

The reaction is advantageously carried out in a polar medium in the presence of a weak base such as $Na_2CO_3$, $Na_3PO_4$ or a mixture of these.

In the preferred embodiments of the process according to the invention, the xanthine ring or xanthine derivative is reacted with a greater than 100% molar excess of substance $X_1$—B—$X_2$.

The molar ratio $X_1$—B—$X_2$/xanthine ring or derivative is, for example, greater than 5 but is preferably greater than or/substantially equal to 10.

Specific examples of compounds of formula $X_1$—B—$X_2$ are 1,2-dichloroethane, 1-chloro-2-bromoethane, 1,2-dibromoethane, 1,3-dichloropropane and 1,3-dibromopropane. The chloro compounds are, however, preferred on account of their better selectivity.

The amount of amine of formula:

used in the reaction of the process according to the invention is itself advantageously chosen such that the molar ratio:

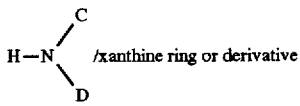

is greater than 1.2, and preferably greater than about 1.5 at the start of the reaction.

The reaction of the process according to the invention may be performed in a solvent, for example a polar or apolar solvent. This solvent, which may be one of the reagents in the reaction (cf. dichloroethane example), is advantageously an ether, a chlorinated solvent, an alkane, an alkanol such as ethanol, propanol, isopropanol, n-pentanol or n-butanol, aromatics such as xylene, dioxane or a mixture of these. In particular, the solvent used will be dioxane or a mixture containing at least 25%, preferably 50%, of dioxane, the remainder of the said mixture consisting of a reagent for the reaction which also acts as a solvent, an alkane, an ether, a chlorinated solvent, an aromatic, an alkanol, xylene or a mixture of these.

It will be noted that dioxane appears to be a compound which promotes the selectivity of the conversion of the xanthine or derivative into

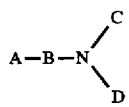

Another subject of the present invention is thus the use of dioxane as a medium for the conversion of the xanthine or derivative into

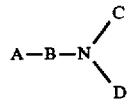

regardless of the temperature or pressure of the reaction.

EXAMPLES

Other characteristic features and details of the invention will emerge from the followed detailed description, in which reference is made to examples of the preparation of xanthine derivatives.

Example 1

The mixture given below is heated at 125° C. for 3 hours in a closed autoclave fitted with a valve for maintaining a constant pressure of +4 bar ($4 \times 10^5$ Pa) therein:

| 15 g | of 8-benzyltheophylline | (0.055 mol) |
| 7.6 g | of 2-ethylaminoethanol | (0.085 mol) |

| 45 ml | of 1,2-dichloroethane | (0.57 mol) |
| 11 g | of anhydrous Na$_2$CO$_3$ | (0.104 mol) |

By monitoring the reaction using liquid phase chromatography (HPLC) or thin layer chromatography, it was observed that conversion of the 8-benzyltheophylline was complete and that the products of the reaction of the nucleophilic ring comprised a minimum of 98% of bamifylline and a maximum of 2% of 7-chloroethyl-8-benzyltheophylline. The reaction mixture was then treated with water to dissolve the inorganic salts. The organic phase was then extracted with hydrochloric acid and then removed.

The acidic aqueous phase was neutralized with sodium carbonate and the [7-(N-ethyl-N-(β-hydroxyethyl)-aminoethyl)]-8-benzyltheophylline was extracted therefrom with a halogenated aliphatic hydrocarbon such as dichloromethane.

After evaporation of the dichloromethane to dryness, the base was dissolved in an alkanol such as methanol and then converted into the hydrochloride by addition of hydrochloric acid. The hydrochloride obtained was purified by crystallization from methanol.

Bamifylline hydrochloride, of melting point 185°–188° C., was obtained in an actual yield of 93%.

Example 2

The following mixture was heated at 125° C. for 5 hours under the conditions described in Example 1:

| 10 g | of 8-benzyltheophylline | (0.037 mol) |
| 5 g | of 2-ethylaminoethanol | (0.056 mol) |
| 30 ml | of xylene | |
| 30 ml | of 1,2-dichloroethane | (0.38 mol) |
| 7.3 g | of anhydrous Na$_2$CO$_3$ | (0.069 mol) |

The reaction was monitored by HPLC, which indicated the absence of 8-benzyltheophylline and the presence of 99.8% of bamifylline and 0.2% of 7-chloroethyl-8-benzyltheophylline.

The solvents were removed under vacuum and the residue was taken up in water. The bamifylline hydrochloride was isolated as described in Example 1.

Example 3

The following mixture was heated at 125° C. for 3 hours under the conditions described in Example 1:

| 10 g | of 8-benzyltheophylline | (0.037 mol) |
| 5 g | of 2-ethylaminoethanol | (0.056 mol) |
| 20 ml | of n-pentanol | |
| 40 ml | of 1,2-dichloroethane | (0.51 mol) |
| 7.3 g | of anhydrous Na$_2$CO$_3$ | (0.069 mol) |

The reaction was monitored by HPLC, which indicated the absence of 8-benzyltheophylline and the presence of 99.4% of bamifylline and 0.6% of 7-chloroethyl-8-benzyltheophylline.

The solvents were removed under vacuum and the residue was taken up in water. The bamifylline hydrochloride was isolated as described in Example 1.

Example 4

Example 2 was repeated, except that dioxane was used as solvent. The conversion of 8-benzyltheophylline into bamifylline was 100%.

Example 5

Example 1 was repeated, except that the reaction was carried out at a temperature of 146° C. instead of 125° C.

The yield of bamifylline observed by HPLC was 97.7% after reaction for 2 hours.

The table below presents the characteristics of Examples 1 to 5 described above which relate to the conversion of 8-benzyltheophylline as a xanthine derivative.

TABLE

| Example No. | Reaction time (hours) | Reagents (moles) | | | | | Selectivity % | | γ | Temp. |
| | | 8-BT | EAE | DCE | BASE | Solvent | X-8-BT % | 7-CE AC-3810 8-BT | AC.-3810 % | °C. |
| --- | --- | --- | --- | --- | --- | --- | --- | --- | --- | --- |
| Comp. | 52 | 0.074 | 0.152 | 0.76 | 0.133 | — | 99.5 | 93     7 | 92.5 | 84° C. |
| 1 | 3 | 0.055 | 0.085 | 0.57 | 0.100 | — | 99.9 |           1.8 | 98.2 | 125° C. |
| 2 | 5 | 0.037 | 0.056 | 0.38 | 0.069 | xylene 30 ml | 99.8 | 98.2 99.8   0.2 | 99.6 | 125° C. |
| 3 | 3 | 0.037 | 0.056 | 0.51 | 0.069 | n-pentanol 20 ml | 99.9 | 99.4     0.6 | 99.2 | 125° C. |
| 4 | 3 | 0.037 | 0.056 | 0.38 | 0.067 | dioxane 30 ml | 100 | 100     0 | 100 | 125° C. |
| 5 | 2 | 0.056 | 0.085 | 0.57 | 0.1 | — | 99.9 | 97.7     1.8 | 97.7 | 146° C. |

8-BT = 8-Benzyltheophylline
Base: Na$_2$CO$_3$
X-8-BT = Percentage conversion of 8-benzyltheophylline (HPLC).
EAE = 2-Ethylaminoethanol
Y-AC3810 = Yield (HPLC) of bamifylline.
DCE = 1,2-Dichloroethane
Selectivity (%) according to HPLC analysis.
AC-3810 = Bamifylline

Example 6

In this example, the process according to the invention was applied to the conversion of theophylline into etamiphylline according to the reaction process below.

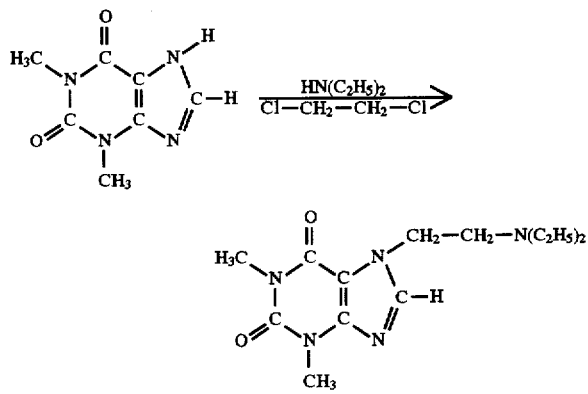

In this example, 10 g of theophylline (0.056 mol), 8.8 ml of diethylamine (0.085 mol), 45 ml of 1,2-dichloroethane (0.57 mol) and 10.6 g of $Na_2CO_3$ (0.1 mol) were reacted together in an autoclave, at a temperature of 125° C. for 3 hours. The reaction temperature was above the reflux temperature of 1,2-dichloroethane, so that the reaction was carried out at a pressure above $10^5$ Pa.

It was determined by HPLC chromatography that the degree of conversion of the theophylline was 97.3%.

The reaction medium was then treated with water and the organic phase was washed using hydrochloric acid solution.

After separation of the organic phase, the pH of the acidic aqueous solution was adjusted to 9.5–10 by addition of sodium carbonate, after which the solution was extracted several times with dichloromethane. After drying, a solid residue of etamophylline was obtained. After a step of crystallization, the melting point of the product was 72° C., this temperature corresponding to the melting point of etamiphylline.

The selectivity of the reaction for etamiphylline was 96.1%.

Example 7

Example 6 was repeated, except that the reaction was carried out at a temperature of 112° C. The degree of conversion of the theophylline was 96.9%, while the selectivity for etamiphylline was 94.2%.

Example 8 (Comparative)

Example 6 was repeated, except that the reaction was carried out in an open reactor supporting a condenser and the reaction temperature was 75° C. A 95% degree of conversion of the theophylline could only be obtained after reaction for 14 hours. The selectivity for etamiphylline was 91.9%.

The table below presents the characteristics of Examples 6 to 8 described above.

| Example | Reaction time (hours) | Temperature °C. | Degree of conversion of the theophylline (%) | Selectivity for etamiphylline (%) |
| --- | --- | --- | --- | --- |
| 6 | 3 | 125 | 97.3 | 96.1 |
| 7 | 3 | 112 | 96.9 | 94.2 |
| 8 | 14 | 75 | 95.2 | 91.9 |

What we claim is:

1. Process for the preparation of bamifylline, in which a mixture comprising:
    a) 8-benzyltheophylline;
    b) an alkyl dihalide with 2 carbon atoms, wherein the molar ratio of said alkyl dihalide to said 8-benzyltheophylline is greater than 5; and
    c) an amine of formula

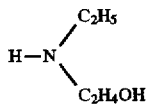

wherein the molar ratio of said amine to said 8-benzyltheophylline is greater than 1.2,
   is reacted in the presence of a weak base selected from the group consisting of $Na_2CO_3$, $Na_3PO_4$, and a mixture thereof, with said reaction carried out in a closed autoclave at a temperature higher than 90° C. and at a pressure higher than $10^5$ Pa.

2. The process of claim 1, in which the reaction is carried out at a temperature higher than 110° C.

3. The process of claim 1, in which the reaction is carried out at a temperature of 125° C.

4. The process of claim 1, in which the alkyl dihalide is 1,2-dichloroethane.

5. The process of claim 1, in which the reaction is carried out with a molar excess of said alkyl dihalide with 2 carbon atoms, and wherein the molar ratio of said alkyl dihalide to said 8-benzyltheophylline is greater than 10.

6. The process of claim 1, in which the reaction is carried out in a solvent selected from the group consisting of ethanol, propanol, isopropanol, n-butanol, n-pentanol, xylene, dioxane, ether, dichloroethane, alkane, and mixtures thereof.

7. The process of claim 6, in which the reaction is carried out with a molar excess of said dichloroethane, and wherein the molar ratio of said dichloroethane to said 8-benzyltheophylline is greater than 5.

8. Process for the preparation of etamiphylline, in which a mixture comprising:
    a) theophylline;
    b) an alkyl dihalide with 2 carbon atoms, wherein the molar ratio of said alkyl dihalide to said is theophylline is greater than 5; and
    c) an amine of formula

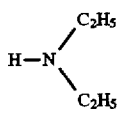

wherein the molar ratio of said amine to said theophylline is greater than 1.2, is reacted in the presence of a weak base, with said reaction carried out in a closed autoclave at a temperature higher than 90° C. and at a pressure higher than $10^5$ Pa.

9. The process of claim 8, in which the reaction is carried out at a temperature higher than 110° C.

10. The process of claim 8, in which the reaction is carried out at a temperature of 125° C.

11. The process of claim 8, in which the alkyl dihalide is 1,2-dichloroethane.

12. The process of claim 8, in which the reaction is carried out with a molar excess of said alkyl dihalide with 2 carbon atoms, and wherein the molar ratio of said alkyl dihalide to said theophylline is greater than 10.

13. The process of claim 8, in which the reaction is carried out in a solvent selected from the group consisting of ethanol, propanol, isopropanol, n-butanol, n-pentanol, xylene, dioxane, ether, dichloroethane, alkane, and mixtures thereof.

14. Process for the preparation of bamifylline, in which a mixture comprising:

a) 8-benzyltheophylline;
b) an alkyl dihalide with 2 carbon atoms, wherein the molar ratio of said alkyl dihalide to said 8-benzyltheophylline is greater than 5; and
c) an amine of formula

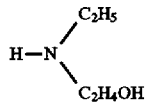

wherein the molar ratio of said amine to said 8-benzyltheophylline is greater than 1.2, is reacted in the presence of a weak base selected from the group consisting of $Na_2CO_3$, $Na_3PO_4$, and a mixture thereof, with said reaction carried out in a closed autoclave at a temperature higher than 90° C. and at a pressure higher than $10^5$ Pa.

15. Process for the preparation of etamiphylline, in which a mixture comprising:

a) theophylline;
b) an alkyl dihalide with 2 carbon atoms, wherein the molar ratio of said alkyl dihalide to said theophylline is greater than 5; and
c) an amine of formula

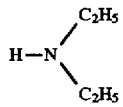

wherein the molar ratio of said amine to said theophylline is greater than 1.2, is reacted in the presence of a weak base selected from the group consisting of $Na_2CO_3$, $Na_3PO_4$, and a mixture thereof, and a solvent selected from the group consisting of ethanol, propanol, isopropanol, n-butanol, n-pentanol, xylene, dioxane, ether, alkane, and mixtures thereof, with said reaction carried out in a closed autoclave at a temperature higher than 90° C. and at a pressure higher than $10^5$ Pa.

* * * * *